United States Patent [19]

Casey et al.

[11] Patent Number: 4,882,168

[45] Date of Patent: * Nov. 21, 1989

[54] POLYESTERS CONTAINING ALKYLENE OXIDE BLOCKS AS DRUG DELIVERY SYSTEMS

[75] Inventors: Donald J. Casey, Ridgefield; Louis Rosati, Norwalk, both of Conn.

[73] Assignee: American Cyanamid Company, Stamford, Conn.

[*] Notice: The portion of the term of this patent subsequent to Dec. 29, 2004 has been disclaimed.

[21] Appl. No.: 903,801

[22] Filed: Sep. 5, 1986

[51] Int. Cl.$^4$ .................. A61K 31/74; C08G 63/08
[52] U.S. Cl. ........................ 424/468; 424/78; 525/415; 528/354
[58] Field of Search ............... 528/354; 525/415; 424/468, 78

[56] References Cited

U.S. PATENT DOCUMENTS

| | | | |
|---|---|---|---|
| 4,300,565 | 11/1981 | Rosensaft et al. | 528/354 |
| 4,429,080 | 1/1984 | Casey et al. | 525/415 |
| 4,526,938 | 7/1985 | Churchill et al. | 525/415 |
| 4,716,203 | 12/1987 | Casey et al. | 528/361 |

Primary Examiner—Joseph L. Schofer
Assistant Examiner—Peter F. Kulkosky
Attorney, Agent, or Firm—Alice C. Brennan

[57] ABSTRACT

The invention is a slow release drug delivery system comprising a drug and an ABA or AB block copolymer wherein one block (B) is a poly(alkylene oxide) and the other blocks (A) are comprised of degradable random copolymers of (1) the cyclic ester of an alpha-hydroxy acid and (2) a second cyclic ester monomer is with the proviso that the second cyclic ester monomer not the same as the first cyclic ester.

15 Claims, No Drawings

POLYESTERS CONTAINING ALKYLENE OXIDE BLOCKS AS DRUG DELIVERY SYSTEMS

The invention is a slow release drug delivery system comprising a drug, preferably bovine somatotropin (bST) and an ABA or AB block polymer wherein the (B) block is a poly(alkylene oxide) and the blocks (A) are comprised of degradable random copolymers of (1) the cyclic ester of an alpha-hydroxy acid and (2) a second cyclic ester monomer with the proviso that the second cyclic ester monomer is not the same as the first cyclic ester. A preferred polymer is one wherein the first cyclic ester of the alpha-hydroxy acid of the block polymer is glycolide and the second cyclic ester monomer is trimethylene carbonate.

The poly(alkylene oxide) concentration in the block polymer is within the range of about 4 to about 54 weight percent of the block polymer and preferably about 4 to about 30 weight percent and the ratio of glycolide to trimethylene carbonate is within a range of about 45 weight percent glycolide and about 55 weight percent trimethylene carbonate to about 68 weight percent glycolide and about 32 weight percent trimethylene carbonate. The average molecular weight of the B component, poly(alkylene oxide), is within a range of about 5000 to about 20,000.

BACKGROUND OF THE INVENTION

Casey et al's U.S. Pat. No. 4,452,973 (1984) teaches the use of poly(glycolide)-PEO-poly(glycolide) ABA polymers as absorbable surgical articles.

Churchill et al's U.S. Pat. No. 4,526,938 (1985) teaches the use of ABA triblock polymers wherein the middle block is polyethylene oxide (PEO) and the end blocks are generally polylactic acid or polyglycolic acid as matrices for the controlled release of drugs.

DESCRIPTION OF THE INVENTION

This invention is degradable thermoplastic hydrogels consisting of ABA or AB block polymers in controlled drug release devices. In an aqueous environment, these materials will swell to a predetermined equilibrium value and will release a wide variety of low and high molecular weight (>1000) biologically active materials. In addition, these materials are capable of being completely degraded and eliminated from the body over a period of time. A particular advantage of these materials is their thermoplastic nature; that is, they can be processed by conventional solution or thermal techniques.

Recently, there has been interest in using hydrogels in a wide variety of biomedical applications such as contact lenses, burn dressings, blood and tissue compatible implants, and drug delivery devices. In the area of controlled drug delivery devices, cross-linked hydrogel materials have met with great success. However, these materials suffer drawbacks, such as a lack of processibility, which are a consequence of their crosslinked nature.

Our approach to this problem was to investigate the use of ABA and AB block copolymers as thermoplastic degradable hydrogels. In these block polymers, the (B) block is a water soluble polymer such as a poly(alkylene oxide) and the blocks (A) are comprised of degradable random copolymers of glycolide (Gly) and trimethylene carbonate (TMC). The middle and end blocks of the block copolymer are chemically incompatible and the result is a phase separated system with crystalline alkylene oxide regions dispersed throughout the Gly/TMC matrix. When exposed to an aqueous environment, the block copolymer segments pick up an amount of water which is a function of the composition and molecular weight of the various block structures. In addition, the low glass transition temperature of the random Gly/TMC blocks allows for facile deformation of the matrix to occur on swelling. This is necessary to accommodate the dimensional changes brought about by the swelling process. The poly(alkylene) oxides are poly($C_2$-$C_4$) oxides. Typically, the polyalkylene oxides used as B blocks include hydroxyl ended polyethylene oxide, hydroxyl ended polyethylene oxide-co-propylene oxide, and the monomethyl ether of the hydroxyl ended polyethylene oxide.

Slow release drug delivery systems of the invention may be used as implants or parenteral suspensions prepared from pharmaceutically and pharmacologically acceptable liquid vehicle.

Polymerization Method

The method of choice for preparing the above ABA triblock copolymers is the melt phase ring-opening copolymerization of glycolide and trimethylene carbonate using specially purified, commercially available difunctional poly(ethylene glycols) as initiators. These polymerizations are conducted in a stirred reactor at 165° C. under nitrogen. When maximum melt viscosity has been reached, the polymer is discharged and allowed to cool to room temperature. The polymers can be purified by reprecipitation from methylene chloride solutions into methanol or ethanol.

Determination of Water Uptake

Samples of the above polymers are extruded at 60-100° C. on an extruded to yield fibers of 1.5 mm average diameter. The fibers are then cut into ~1" lengths and several are placed in deionized water at room temperature. At various time intervals, the fibers are withdrawn, wiped thoroughly to remove any surface liquid, and the water uptake is measured gravimetrically. Alternatively, the uptake can be measured with thin films (~0.6 mm) prepared by compression molding the polymer at 90° C., or by casting thin films of the polymer from solution.

Fabrication Methods

A. Solution Casting

A solution of polymer (20-50% w/v) is prepared in an appropriate low boiling solvent such as methylene chloride. A biologically active material that is insoluble in methylene chloride, such as bovine somatotropin (bST), is added with rapid stirring to form a viscous slurry. The proportions are chosen so that the active material is 1-75% of the weight of the final dry device. The slurry is then poured into a mold which has been pre-cooled to −78° C. After approximately 15 minutes, the frozen slab is placed in a freezer for 3-4 days to allow most of the solvent to evaporate. Final drying of the solution cast disk is accomplished in a vacuum oven at room temperature. The disk can be cut into squares or, in the preferred method, cryogenically ground through a 20 mesh screen to give particles which are capable of being injected or implanted.

B. Coextrusion

The above polymers and a biologically active material are coextruded at 60-115° C. on a laboratory scale extruder. The ratio of active material is chosen to be 1-50% w/w but is preferably 25-50% w/w. The 1.5 mm diameter fibers can be cut into lengths or cryogenically ground through a 20 mesh screen to give particles which are capable of being injected, or the fiber can be directly implanted.

In Vitro Release Measurements

A sample (0.5-2.5 g) of polymer which had been loaded with a biologically active material such as bST is placed into a polypropylene dissolution tube. To simulate physiological conditions, 30 ml of phosphate buffered saline at pH=7.4 is added and the tube is capped. The dissolution tube is then rotated at 3-7 rpm in a water bath at 37° C. Periodically, an aliquot of solution is removed and replaced by fresh buffered saline. The aliquot is then analyzed for total protein content by using a biuret assay. The protein copper complex is measured spectrophotometrically at 540 nm and is compared to a calibration curve constructed with known amounts of an identical protein. In the preferred method, the entire buffer solution is decanted daily from the dissolution tube and replaced by 30 ml of fresh buffer solution. An aliquot of the decanted buffer solution is then analyzed by the biuret assay method as above.

In Vivo Release Measurements

Polymer which contains bST is ground through a 20 mesh screen and suspended in soybean oil. Six hypophysectomized (hypox) rats are injected with the polymer containing the bST. The amount injected is adjusted so that each animal receives 800 ug of bST. In addition, there are two control groups of six hypox rats. The first group (positive control) each receives 80 ug of bST in buffer daily for 10 days (800 ug total). The second control group receives daily injections of aqueous buffer (negative control). The average weight gains of the 3 groups are then measured over a 10-day period.

EXAMPLE 1

Purification of Materials

DL-lactide: DL-lactide was purchased from Purac, Inc. One kilogram of DL-lactide is refluxed for 1 ½ hours with toluene (1500 g) which has been dried by distillation from benzophenone ketyl. The residual water is removed from the DL-lactide by collection of the toluene/water azeotrope in a Dean-Stark trap. The dry DL-lactide solution is allowed to cool to room temperature and placed in the refrigerator overnight. The crystallized DL-lactide is then quickly filtered and dried in a vacuum oven at room temperature. Recrystallization yield is 84%.

Polyethylene Glycol-8,000: Polyethylene glycol-8,000 (PEG 8,000) (160 g) is dissolved in methanol (1600 ml). The PEG solution is then freed of catalyst impurities and deionized by slowly passing the solution through a methanol conditioned indicating mixed bed anionic and cationic ion-exchange resin (Amberlite MB-3, Rohm and Haas Company, Pennsylvania, U.S.A.). After elution from the column, the PEG is crystallized by placing the solution in a freezer overnight. The crystalline PEG is then filtered and air dried for 2 hours. The PEG is further purified by recrystallization from acetone (1600 ml). The recrystallized PEG is filtered and dried in a vacuum oven at room temperature overnight. Prior to polymerization, the desired amount of purified PEG is dried further by heating in a vacuum oven at 70° C. with $P_2O_5$ as a desiccant. PEG-14,000 and PEG-20,000 are purified in the same way.

Pluronic F68: Pluronic F68 was purified by the same technique as described for PEG above but without the acetone recrystallization step. The methanol recrystallized Pluronic F68 was filtered and dried in a vacuum oven at room temperature. Prior to polymerization, the Pluronic F68 was further dried by heating in a vacuum oven at 70° C. with $P_2O_5$ as a desiccant.

Pluronic P105: Pluronic P105 was purified by the same method described for PEG above. The polymer was recovered from the methanol solution using a rotary evaporator. Residual methanol was removed by drying in vacuum to constant weight. The material was not recrystallized from acetone. Prior to polymerization the Pluronic P105 was dried further by heating in a vacuum oven at 50° C. with $P_2O_5$ as a desiccant.

Polyethylene Glycol Methyl Ether: Polyethylene glycol methyl ether, nominal molecular weight 5000, was purified in the same way as described for PEG above.

EXAMPLE 2

Synthesis of (Gly/TMC)-(PEO 14,000)-(Gly/TMC) ABA Triblock Copolymer (Gly/PEO/TMC: 34/41/25)

A 250 ml flask is charged with PEG-14000 (50 g, 0.0036 mole). The flask is placed in a vacuum oven and the PEG is dried overnight under vacuum at 70° C. with $P_2O_5$ as a drying agent. The flask is then placed in a glove bag under $N_2$. Glycolide (25.0 g, 0.21 mole) and trimethylene carbonate (25.0 g, 0.24 mole) are charged to the flask and the contents are melted and mixed under $N_2$. The monomer mixture is then quickly transferred into a stirred reactor which has been heated under a nitrogen flow to 165° C. Stannous octoate (0.16 ml, $4.9 \times 10^{-4}$ mole) is then quickly charged to the reactor with the use of a syringe. The polymer melt is stirred at 40 rpm for approximately 3 hours at 165° C. This time period corresponds to a maximum in the melt viscosity. The polymer is discharged from the reactor and allowed to cool to room temperature. A portion of the crude polymer (42.8 g) is dissolved in $CH_2Cl_2$ (250 ml) and reprecipitated dropwise into rapidly stirred absolute ethanol (3000 ml). After filtration and drying to constant weight, the reprecipitation yield was determined to be 96%. The inherent viscosity of the polymer (0.5%, in $CHCl_3$ at 30° C.) was 0.38 dL/g. The composition was analyzed by $^1$H-NMR and was found to be 34/41/25 weight percent Gly/PEO/TMC. The Tg of the polymer was 11° C., the melting point (Tm) was 59° C.

EXAMPLES 3-14

Several polymers were prepared as in Example 2 with varying PEG contents and PEG molecular weights (Table I). In many of the Gly/PEO/TMC triblock copolymers, the charged ratio of Gly/TMC is 60/40 weight percent. This allows for maximum Tg of the rubbery end blocks while still maintaining solubility in common organic solvents. Differential scanning calorimetry (DSC) clearly shows phase separation in these materials. The Tg of the rubbery end blocks (7-16° C.)

is very close to the Tg of a 60/40 random Gly/TMC polymer. In addition, the Tm of the crystalline PEO segments are only lowered 5-10° C.

EXAMPLE 15

Synthesis of (Gly/TMC)-(PEO-8000)-Gly/TMC) ABA, (Gly/PEO/TMC: 59/6/35)

Glycolide (117.0 g, 1.01 mole), trimethylene carbonate (71.0 g, 0.70 mole), PEG-8000 (12.0 g) and stannous octoate (0.33 ml $1.0 \times 10^{-3}$ mole) were combined in a stirred reactor as in Example 2. The reaction mixture was then stirred at 169° C. and 36-40 rpm for 1.5 hours. The polymer was recovered as in Example 2. The properties of this polymer are summarized in Table I.

EXAMPLE 16

Synthesis of (Gly/TMC)-(PEO-8000)-(Gly/TMC) ABA, (Gly/PEO/TMC: 54/8/38)

Glycolide (110.4 g, 0.95 moles), trimethylene carbonate (73.6 g, 0.72 moles), PEG-8000 (16.0 g) and stannous octoate (0.32 ml, $9.96 \times 10^{-4}$ moles) were combined and allowed to polymerize as in Example 15. The properties of this polymer as summarized in Table I.

EXAMPLE 17

Synthesis of (Gly/TMC)-(PEO-8000)-(Gly/TMC) ABA, (Gly/PEO/TMC: 54/10/36)

Glycolide (108.0 g, 0.93 moles), trimethylene carbonate (72.0 g, 0.71 moles), PEG-8000 (20.0 g) and stannous octoate (0.32 ml, $9.96 \times 10^{-4}$ moles) were combined and allowed to polymerize as in Example 15. The properties of this material are summarized in Table I.

ml, $9.96 \times 10^{-4}$ moles) were combined and allowed to polymerize as in Example 2. The properties of this polymer are summarized in Table II.

EXAMPLE 19

Synthesis of (Gly/l-Lact)-(PEO-8000)-(Gly/l-Lact) ABA: (Gly/l-Lact/PEO: 27/65/8)

Glycolide (53.2 g, 0.46 moles), l-lactide (130.8 g, 0.91 moles), PEG-8000 (16.0 g) and stannous octoate (0.05 ml, $1.56 \times 10^{-4}$ moles) are combined and allowed to polymerize by the procedure described in Example 15. The properties of this polymer are summarized in Table II.

EXAMPLE 20

Synthesis of (l-Lact/TMC)-(PEO-8000)-(l-Lact/TMC) ABA, (l-Lact/TMC/PEO: 43/49/8)

l-Lactide (88.0 g, 0.61 moles), trimethylene carbonate (96.0 g, 0.94 moles), PEG-8000 (16.0 g) and stannous octoate (0.31 ml, $9.74 \times 10^{-4}$ moles) are combined and allowed to polymerize by the procedure described in Example 15. The properties of this polymer are summarized in Table II.

EXAMPLE 21

Synthesis of (Gly/dl-Lact)-(PEO-20,000)-(Gly/dl-Lact) ABA, (Gly/dl-Lact/PEO: 21/25/54)

dl-lactide (25.0 g, 0.17 moles), glycolide (25.0 g, 0.21 moles), PEG 20,000 (50.0 g) and stannous octoate (0.16 ml, $4.94 \times 10^{-4}$ moles) are combined and allowed to polymerize by the procedure described in Example 2.

TABLE I

Glycolide/PEO/TMC Polymers

| | Charged Composition | | ηinh (Solvent) | | Gly/PEO/TMC Composition by $^1$H-NMR (wt %) | | | |
|---|---|---|---|---|---|---|---|---|
| Ex. | (Gly/PEO/TMC Wgt. %) | PEG MW | As Polymerized | Reprecipitated | As Polymerized | Reprecipitated | Tg (°C.) | Tm (°C.) |
| 3 | 25/50/25 | 14,000 | — | 0.40 (CHCl$_3$) | — | 30/43/27 | — | — |
| 4 | 32/50/18 | 14,000 | — | 0.45 (CH$_2$Cl$_2$) | — | 31/54/15 | — | — |
| 5 | 48/20/32 | 14,000 | — | 0.45 (CHCl$_3$) | — | 49/19/32 | 16 | 57 |
| 6 | 54/10/36 | 14,000 | — | 0.34 (CH$_2$Cl$_2$) | — | 55/11/34 | 12 | 54 |
| 7 | 42/30/28 | 14,000 | 0.45 (CH$_2$Cl$_2$) | 0.45 (CH$_2$Cl$_2$) | — | 44/29/27 | 15 | 58 |
| 8 | 42/30/28 | 8,000 | 0.40 (CH$_2$Cl$_2$) | 0.38 (CH$_2$Cl$_2$) | — | 43/31/26 | 16 | 55 |
| 9 | 48/20/32 | 8,000 | 0.42 (CH$_2$Cl$_2$) | — | 48/21/31 | — | 14 | 55 |
| 10 | 54/10/36 | 8,000 | 0.46 (CH$_2$Cl$_2$) | 0.33 (CHCl$_3$) | 50/10/40 | 50/8/42 | 10 | 53 |
| 11 | 54/10/36 | 20,000 | — | — | — | — | 7 | 47 |
| 12 | 48/20/32 | 20,000 | — | — | — | — | 6 | 52 |
| 13 | 42/30/28 | 20,000 | — | — | — | — | 11 | 54 |
| 14 | 57/5/38 | 8,000 | 0.41 (CHCl$_3$) | 0.38 (CHCl$_3$) | 57/5/38 | 58/5/37 | — | — |
| 15 | 58/6/36 | 8,000 | 0.42 (CHCl$_3$) | 0.40 (CHCl$_3$) | 59/6/35 | 59/6/35 | — | — |
| 16 | 55/8/37 | 8,000 | 0.44 (CHCl$_3$) | 0.42 (CHCl$_3$) | 53/8/39 | 54/8/38 | — | — |
| 17 | 54/10/36 | 8,000 | 0.45 (CHCl$_3$) | 0.40 (CHCl$_3$) | 54/10/36 | 54/10/36 | — | — |

EXAMPLE 18

Synthesis of (Gly/dl-Lact)-(PEO-8000)-(Gly/dl-Lact) ABA, (Gly/dl-Lact/PEO: 36/54/10)

Glycolide (54.0 g, 0.46 moles), dl-lactide (81.0 g, 0 56 moles), PEG-8000 (15.0 g) and stannous octoate (0.32

The properties of this polymer are described in Table II.

TABLE II

Terpolymers With PEO Midblocks and Various Endblocks

| Ex. | Charged Composition | PEG MW | ΔInh (Solvent) As Polymerized | ΔInh (Solvent) Reprecipitated | Composition by $^1$H-NMR (Wt %) As Polymerized | Composition by $^1$H-NMR (Wt %) Reprecipitated | Tg | Tm |
|---|---|---|---|---|---|---|---|---|
| 18 | Gly/dl-lactide/PEO: 36/54/10 | 8,000 | 0.49 ($CHCl_3$) | 0.35 ($CHCl_3$) | 36/54/10 | 36/54/10 | — | — |
| 19 | Gly/l-lactide/PEO: 27/65/8 | 8,000 | 0.73 ($CHCl_3$) | — | 27/65/8 | — | 36 | — |
| 20 | l-Lactide/TMC/PEO: 44/48/8 | 8,000 | 0.56 ($CHCl_3$) | — | 43/49/8 | — | 0 | — |
| 21 | Gly/dl-lactide/PEO: 25/25/50 | 20,000 | — | 0.43 ($CHCl_3$) | — | 21/25/54 | 42 | 57 |

EXAMPLE 22

Swelling Behavior of Examples 3, 4 and 21

A film was prepared by solution casting a 20% w/v solution of the polymer of Example 3 in $CH_2Cl_2$. After the solvent had evaporated overnight, the film was dried further under vacuum at room temperature overnight. Films made from the polymers of Example 3, 4 and 21 were placed in water at 37° C. with stirring. After 24 hours, films from Example 3 and Example 4 had formed emulsions. By day 3, the film from Example 21 had also formed an emulsion.

EXAMPLE 23

Swelling Behavior of Example 7 (Gly/PEO/TMC: 44/29/27)

A sample of the polymer from Example 7 (1.5 g) was extruded at 110° C. on an extruded to yield a 1.5 mm diameter fiber. From the fiber 5 samples, lengths each approximately 1″ were cut. The samples were placed in deionized water at room temperature. Periodically, the samples were withdrawn, wiped dry, and the water uptake measured gravimetrically. The water uptake is shown in Table III. From the values at 1280 min., the equilibrium water uptake for fibers was calculated to be 232 ±3%.

The same type of water uptake analysis was performed on 4 samples of films of the polymer of Example 7 (12×4×0.6 mm). The results are shown in Table III.

The shorter time to reach an equilibrium value of water uptake in the films is attributable to the greater surface-to-volume ratio in the films.

TABLE III

Water Uptake by Fibers and Films of 44/29/27 Gly/PEO/TMC (Ex. 7)

| Fibers Time (min) | Fibers % $H_2O^A$ Uptake | Films Time (min) | Films % $H_2O^A$ Uptake |
|---|---|---|---|
| 5 | 31.1 | 5 | 136.7 |
| 18 | 60.9 | 22 | 238.7 |
| 32 | 89.3 | 35 | 271.0 |
| 45 | 107.9 | 63 | 279.5 |
| 65 | 133.6 | 81 | 282.2 |
| 90 | 158.2 | 216 | 279.1 |
| 118 | 183.7 | 363 | 253.5 |
| 148 | 204.3 | 1560 | 266.3 |
| 179 | 223.3 | | |
| 1155 | 237.6 | | |
| 1280 | 235.5 | | |

$$A = \frac{(Wt\ Swollen - Wt\ Dry)}{Wt\ Dry} \times 100$$

EXAMPLE 24

Swelling of Various Hydrogels

Water uptake experiments were carried out on fibers of several Gly/PEO/TMC hydrogels and one Gly/dl-Lactide/PEO hydrogel (Table IV). Measurements were carried out at room temperature in deionized water. All reported equilibrium uptake values are averages of 4 or 5 samples.

TABLE IV

Combined Swelling Data on Polymers

| Example | Polymer | PEG MW | PEO Content (Wgt. %) | % $H_2O$ Uptake | Teg |
|---|---|---|---|---|---|
| 14 | Gly/PEO/TMC | 8,000 | 5 | 27.9 ± 5.4[1,3] | 13 days |
| 10 | Gly/PEO/TMC | 8,000 | 8 | 124.1 ± 7.4[1,3] | 1 day |
| 10 | Gly/PEO/TMC | 8,000 | 10 | 11.3 ± 0.9[1,2] | 4 |
| 18 | Gly/dl-lactide/PEO | 8,000 | 10 | 9.9 ± 1.3[1,3,5] | 5 |
| 9 | Gly/PEO/TMC | 8,000 | 21 | 163.0 ± 1.8[1,2] | 4 |
| 8 | Gly/PEO/TMC | 8,000 | 31 | 224.5 ± 15.1[1,2] | 4 |
| 6 | Gly/PEO/TMC | 14,000 | 11 | 125.8 ± 4.5[1,3] | 4 |
| 5 | Gly/PEO/TMC | 14,000 | 19 | 164.9 ± 11.2[1,3] | 4 |
| 7 | Gly/PEO/TMC | 14,000 | 29 | 235.9 ± 3.1[1,3] | 17 hrs. |
| 7 | Gly/PEO/TMC | 14,000 | 29 | 260.8 ± 10.3[3,6] | 20 min. |
| 11 | Gly/PEO/TMC | 20,000 | 10 | 61.0 ± 0.5[1,2] | 4 |
| 12 | Gly/PEO/TMC | 20,000 | 20 | 169.0 ± 0.8[1,2] | 4 |
| 13 | Gly/PEO/TMC | 20,000 | 30 | 289.2 ± 5.6[1,2] | 4 |

1 = fiber (dimensions = 10 mm × 1.5 mm diameter)
2 = as polymerized
3 = reprecipitated
4 = not determined
5 = not at equilibrium by day 13
6 = film (dimensions = 12 × 4 × 0.6 mm)

Several generalizations about the data in Table IV can be made. The time to reach an equilibrium value of water uptake depends on the shape of the sample (Example 7 fiber vs. film). It would also appear that the time to reach an equilibrium value of water uptake decreases as the PEO content increases.

Within the scatter in the data, equilibrium water uptake is linearly related to the PEO content in the range 5–30%. There is no noticeable effect of the MW of the PEO block on the swelling of these triblock polymers (within the range of PEO MW 8,000–20,000).

One important difference noted in Table IV is the contrast of Example 10 (Gly/PEO/TMC) with Example 18 (Gly/PEO/dl-Lactide). Both have approximately the same percent of PEO 8,000; however, a reprecipitated sample of Example 10 had an equilibrium water content of 124% (Teg 1 day) vs. 9.9% by day 13 for a reprecipitated sample of Example 18. The difference can be rationalized by looking at the differences of the two matrices. In the case of the sample of Example 10 the rubbery Gly/TMC matrix is free to deform to accommodate the dimensional changes caused by the swelling. In Example 18 however the Gly/dl-Lactide matrix is in a glassy state. This should result in a slower water uptake curve (note that at 13 days equilibrium has not been reached) until the Gly/dl-Lactide matrix is sufficiently plasticized by water.

EXAMPLE 25

Synthesis of (Gly/TMC) [Pluronic F68] (Gly/TMC) ABA (Gly/Pluronic F68/TMC: 56/8/36) Multiblock Copolymer Pluronic F68 (BASF Wyandotte, U.S.A.) is a triblock copolymer of poly(ethylene oxide) (PEO) (80 mole %) and poly(propylene oxide) (PPO) (20 mole %) where PPO forms the middle block and the total molecular weight is about 8400. Like PEO, this copolymer is terminated with hydroxyl groups which can be used as an initiator for the ring opening polymerization of cyclic esters.

Glycolide (82.8 g), trimethylene carbonate (55.2 g) Pluronic F68 (12.0 g) and stannous octoate (0.242 ml), where combined in a stirred reactor as in Example 2. The reaction mixture was then stirred at 165° C. and 40 rpm for 1.5 hours. The polymer was recovered as in Example 2 and then characterized as follows:

$\eta$Inh (CHCl$_3$):0.40; Composition: 56/8/36 ($^1$H-NMR); Tg:14° C.; Tm 42° C.

EXAMPLE 26

Synthesis of (Gly/TMC) [Pluronic P105] (Gly/TMC) ABA (Gly/Pluronic P105/TMC: 56/9/35) Multiblock Copolymer Pluronic P105 (BASF Wyandotte, USA) is triblock copolymer of poly(ethylene oxide) (PEO) (50 mole %) and poly(propylene oxide) (PPO) (50 mole %) where PPO forms the middle block and the total molecular weight is about 6500. Like PEO, this copolymer is terminated with hydroxyl groups which can be used as an initiator for the ring opening polymerization of cyclic esters.

Glycolide (54 g), trimethylene carbonate (36 g) Pluronic F68 (10.0 g) and stannous octoate (0.19 ml), where combined in a stirred reactor as in Example 2. The reaction mixture was then stirred at 165° C. and 40 rpm for 1.5 hours. The polymer was recovered as in Example 2 and then characterized as follows:

$\eta$Inh (CHCl$_3$):0.35; Composition: 56/9/35 ($^1$H-NMR).

EXAMPLE 27

Synthesis of (PEO)-(Gly/TMC) AB (Gly/PEO/TMC: 57/6/37) Diblock Copolymer

Poly(ethylene glycol) methyl ether (PEO-5000) was purchased from Aldrich Chemical Company. The molecular weight was reported to be 5000. This polymer is terminated by one hydroxyl group and one methyl ether group. Only one end of this molecule, therefore, can be used to initiate the ring opening polymerization of cyclic esters, forming an AB diblock copolymer.

Glycolide (84.6 g), trimethylene carbonate (54.4 g) PEO 5000 (10.0 g) and stannous octoate (0.242 ml), where combined in a stirred reactor as in Example 2. The reaction mixture was then stirred at 165° C. and 40 rpm for 1.5 hours. The polymer was recovered as in Example 2 and then characterized as follows:

$\eta$Inh (CHCl$_3$):0.42; Composition: 57/6/37 ($^1$H-NMR); Tg:12° C.; Tm:59° C.

EXAMPLE 28

In Vitro Release of Theophylline (30% w/w loaded hydrogel)

Theophylline and hydrogel Example 10 [Gly/PEO 8,000/TMC (50/8/42] were mixed and extruded at 80° C. on a laboratory scale extruder. The loading of theophylline was 30% w/w. To a 2,000 ml 24/40 erlemeyer flask, 0.2939 g of the hydrogel formulation, 882 ml of phosphate buffer (pH 6.89) and a magnetic stirring bar were charged. The flask was quickly placed into a 39° C. water bath and stirring was started with the use of a submersible water driven stir plate. A peristaltic pump was used to circulate the buffer solution through a flowthrough UV cell and theophylline release was monitored by following the absorbance in the region 284–287 nm. The fractional release for the 30% loaded hydrogel Example 10 is given in Table V. The release curve is typical of release from a matrix type device. Release from this type of device would be expected to follow a t$^{\frac{1}{2}}$ dependence (linear with square root of time) on the release rate. When plotted versus the square root of time, release is linear up to 85–90% of the total fractional release.

TABLE V

| Theophylline Release from 30% Loaded Hydrogel Example 10 | |
| --- | --- |
| Time (min) | Percent Released |
| 8 | 9.3 |
| 13 | 18.7 |
| 18 | 24.0 |
| 23 | 30.7 |
| 30 | 36.0 |
| 36 | 40.0 |
| 51 | 52.0 |
| 66 | 61.3 |
| 81 | 68.0 |
| 96 | 73.3 |
| 111 | 77.3 |
| 141 | 84.0 |
| 186 | 89.3 |
| 249 | 93.3 |
| 429 | 97.3 |
| 819 | 98.7 |
| 1149 | 100.0 |

EXAMPLES 29-31

Theophylline Release from 20, 10 and 5% Loaded Hydrogel of Example 10

Release of theophylline from hydrogel of Example 10 at 20%, 10% and 5% w/w loadings was carried out in the same manner as in Example 28. For this system, the release rates were very similar for loadings in the range of 5-20% with 100% of the theophylline released over a 13-15 hour period.

EXAMPLE 32

Theophylline Release from 5% Loaded Hydrogel of Example 14

Release of theophylline from 5% loaded hydrogel Example 14 (Gly/PEO 8,000/TMC 58/5/37) showed a much lower release rate as compared to hydrogel Example 10 (Table VI). This is attributable to the differences in swelling behavior of the two polymers. Hydrogel Example 10 (due to its higher PEO content) reaches an equilibrium water content of 124% in 24 hours. On the other hand, hydrogel Example 14 with only 5% PEO picks up approximately 28% water in a 13 day period.

TABLE VI

Theophylline Release from 5% Loaded Hydrogel Example 14

| Time (hrs) | Percent Released |
|---|---|
| 0.5 | 2.0 |
| 1.12 | 2.3 |
| 4.65 | 2.4 |
| 7.6 | 2.6 |
| 10.6 | 3.4 |
| 25.15 | 6.7 |
| 46.15 | 7.3 |
| 63.15 | 7.9 |
| 82.15 | 8.2 |

EXAMPLES 33-44

In Vitro Release of bST at 37° C., pH=7.4

In vitro release of bST was measured for a number of hydrogel compositions (Table VII) and fabrication methods. The results indicate that, in general, bST release rates increase as the PEO content of the hydrogel increases. As previously discussed, higher PEO content leads to increased equilibrium water uptake which should allow for faster bST diffusion through the swollen gel. Several other trends are apparent from the results in Table VII. The fabrication method greatly influences the release rates of bST from the hydrogels. In general, it was found that extruded fibers gave lower release rates than solution cast films. The cast films contained a large number of voids and often delaminated due to the drying process. This gave a formulation with a much higher surface to volume ratio as compared to the extruded fibers. This high surface/volume ratio accounts for the high release after only 1 day for the solution cast films.

No discernible differences in release rates as a function of PEO mw could be detected. Again, this is expected as it previously has been shown that, in the mw range studied, PEG mw did not influence the swelling behavior of the hydrogels. Finally, it has been demonstrated that release rates can be modified by blending various additives into the formulations. A blend of bST/hydrogel (Example 10) and a Gly/L-lactide (40/60) polymer $\eta$inh=0.50 (25/50/25) was extruded. The measured in vitro release rate of the blend was approximately ⅔ of the release rate for the hydrogel. By blending in a non-swelling Gly/L-lactide polymer, it serves to lower the overall PEO content and reduce the water uptake of the hydrogel. The measured release rates can also be increased by blending in a water soluble filler. When sorbitol was added to the previously described blend, the measured release rates were greater than the parent hydrogel release rates. The water soluble filler is leached out into the dissolution media leaving a more porous matrix which facilitates the release of the active material.

TABLE VII

| | | | | | | In Vitro Release of bST 37° C., pH 7.4 | | | | | |
|---|---|---|---|---|---|---|---|---|---|---|---|
| Example No. | Polymer Example | PEG MW | PEG Content (wt %) | bST Loading | Fabrication Method[C] | Day | | | | | |
| | | | | | | 1 | 2 | 3 | 4 | 5 | 6 |
| 33 | 10 | 8,000 | 8 | 25 | SC | 76.9 | 78.5 | — | — | — | 79.1 |
| 34 | 10 | 8,000 | 8 | 25 | EX | 22.1 | 30.2 | — | — | 31.2 | 32.7 |
| 35 | 10 | 8,000 | 8 | 25[A] | EX | 14.4 | 17.1 | — | — | 20.2 | 20.2 |
| 36 | 10 | 8,000 | 8 | 25[B] | EX | 38.0 | 41.9 | — | — | — | 36.9 |
| 37 | 9 | 8,000 | 21 | 25 | SC | 75.6 | 78.8 | — | — | — | 77.8 |
| 38 | 8 | 8,000 | 31 | 25 | SC | 76.0 | 88.2 | 77.4 | — | — | 89.2 |
| 39 | 6 | 14,000 | 11 | 25 | SC | 60.2 | 67.4 | 66.4 | — | — | 77.9 |
| 40 | 5 | 14,000 | 19 | 25 | SC | 75.0 | 76.6 | — | — | — | 79.0 |
| 41 | 7 | 14,000 | 29 | 25 | SC | 84.0 | 84.7 | — | — | — | 86.7 |
| 42 | 11 | 20,000 | 10 | 25 | EX | — | 37.6 | — | — | 58.6 | — |
| 43 | 12 | 20,000 | 20 | 25 | EX | 61.9 | 78.9 | — | — | 78.8 | — |
| 44 | 13 | 20,000 | 30 | 25 | EX | 39.6 | 61.2 | — | — | 85.5 | — |

A = Formulation is a blend (25% bST/50% Ex. 10/25% Gly/L-lace $\eta$inh = 0.50
B = Formulation is a blend (25% bST/25% Ex. 10/25% sorbitol/25% Gly/L-lace $\eta$inh = 0.50
C = EX = extruded
SC = solution cast

EXAMPLE 45

In Vitro Release of bST at 37° C., pH=9.4

Accelerated in-vitro release of bST was measured from fibers of the polymer Example 26. Polymer plus bST (40% loading) were extruded as in Example 33. It was found that this formulation released bST continuously over at least a 22 hour period at pH 9.4 and 37° C.

EXAMPLE 46 In-vitro Release of bST at 37° C., pH=9.4

Accelerated in-vitro release of bST was measured from fibers of the polymer of Example 27. Polymer plus bST (40% loading) were extruded as in Example 33. It was found that this formulation released bST continuously over at least a 22 hour period at pH 9.4 and 37° C.

EXAMPLES 47–48

In Vivo Release of bST in Hypox Rats Based on the in vitro release curves, two formulations were tested for in vivo release of bST in hypox rats. The experimental details of the in vivo measurements were discussed previously. The results are shown in Table VIII. Both formulations show growth in hypox rats throughout the 10 day test period.

TABLE VIII

In Vivo Release Data
25% bST Loaded Ground Matrices

| Ex. No. | % PEO | PEO MW | Weight Gain (grams) | | |
|---|---|---|---|---|---|
| | | | 0–3 Days | 0–7 Days | 0–10 Days |
| 47 | 10 | 8,000 | 5.6 ± 1.0 | 10.0 ± 1.4 | 12.3 ± 1.5 |
| 48 | A | A | 8.8 ± 0.86 | 13.8 ± 1.9 | 15.6 ± 2.0 |
| | Control[B] | | 8.6 ± 1.3 | 15.8 ± 1.3 | 25.5 ± 1.7 |

A = Blend 33% [Example 10]
67% [(Gly/lact) 40/60 $\eta$inh = 0.50]
B = 10 injections (80 μg/day)

We claim:
1. A slow release drug delivery system comprising a drug and
an ABA or AB block polymer wherein the (B) block is a poly(alkylene oxide) having an average molecular weight in a range of about 5,000 to about 20,000 and the blocks (A) are comprised of degradable random copolymers of (1) the cyclic ester of an alpha-hydroxy acid and (2) trimethylene carbonate; wherein said block polymer has a glass transition temperature at or less than 16° C.

2. A drug delivery system according to claim 1 wherein the polymer is an ABA block polymer, and the first cyclic ester is glycolide.

3. A drug delivery system according to claim 2 wherein the B block is polyethylene oxide or polyethylene oxide-co-propylene oxide.

4. A drug delivery system according to claim 2 wherein the poly(ethylene oxide) comprises from about 4 to about 54 weight % of the ABA polymer and the ratio of glycolide to trimethylene carbonate components is within a range of 45 weight % glycolide and 55 weight % trimethylene carbonate to 68% weight % glycolide and 32 weight % trimethylene carbonate.

5. A drug delivery system according to claim 4 wherein the drug is bovine somatotropin and the poly(ethylene oxide) comprises from about 4 to about 30 weight % of the ABA polymer.

6. A drug delivery system according to claim 4 wherein average molecular weight of the poly(ethylene oxide) is within a range of 6,000–20,000.

7. A drug delivery system according to claim 6 wherein the bovine somatotropin comprises from about 10 to about 40 weight % of the system.

8. A drug delivery system according to claim 7 wherein the bovine somatotropin comprises about 25 weight % of the system.

9. A drug delivery system according to claim 8 wherein the average molecular weight of the poly(ethylene oxide) is 8000.

10. A drug delivery system according to claim 8 wherein the average molecular weight of the poly(ethylene oxide) is 14,000.

11. A drug delivery system according to claim 8 wherein the average molecular weight of the poly(ethylene oxide) is 20,000.

12. A drug delivery system according to claim 4 wherein the drug is theophylline and the poly(ethylene oxide) comprises from about 4 to about 30 weight % of the ABA polymer.

13. A slow release drug delivery system according to claim 1 suspended in a pharmaceutically or pharmacologically acceptable liquid vehicle.

14. A drug delivery system according to claim 1 wherein the polymer is an AB block polymer and the first cyclic ester is glycolide.

15. A drug delivery system according to claim 14 wherein the B block is a monomethyl ether of a hydroxyl ended polyethylene oxide.

* * * * *